United States Patent [19]

Cramer et al.

[11] 4,109,509
[45] Aug. 29, 1978

[54] OXYGEN MONITOR AND WARNING DEVICE FOR AN AIRCRAFT BREATHING SYSTEM

[75] Inventors: Robert L. Cramer; John W. Henneman, both of Davenport, Iowa

[73] Assignee: The Bendix Corporation, Southfield, Mich.

[21] Appl. No.: 838,278

[22] Filed: Sep. 30, 1977

[51] Int. Cl.² .................. G01N 31/00; A62B 7/14
[52] U.S. Cl. .................................. 73/23; 128/142 R
[58] Field of Search ................ 73/23, 19, 386, 387; 128/140 R, 142 R

[56] References Cited

U.S. PATENT DOCUMENTS

| | | | |
|---|---|---|---|
| 3,309,684 | 3/1967 | Kahn et al. | 73/23 |
| 3,507,146 | 4/1970 | Webb | 73/23 |
| 3,521,627 | 7/1970 | Murray | 128/142 R |
| 3,572,331 | 3/1971 | Kissen | 128/142 R |
| 3,788,310 | 1/1974 | Fleischmann | 128/142 R |

*Primary Examiner*—Stephen A. Kreitman
*Attorney, Agent, or Firm*—Leo H. McCormick, Jr.; Ken C. Decker

[57] ABSTRACT

In an aircraft breathing system a sensor assembly for monitoring the concentration of oxygen in a source of breathable fluid supplied to a recipient. The sensor assembly has a housing with a chamber therein connected by a conduit to the source of breathable fluid. A restricted orifice member in the conduit allows a sample of the breathable fluid to continually flow into the chamber while an exit port in the housing allows the sample of breathable fluid to flow to the surrounding environment. A sensor responsive to the partial pressure of oxygen is connected to the chamber. The sensor in response to the partial pressure of the oxygen produces an operational signal. The operational signal activates an indicator to provide the recipient with a reading of the concentration of oxygen in the breathable fluid. An aneroid fixed to the housing has a face that engages a seat surrounding the exit port. Whenever the aircraft is above a predetermined altitude to establish a constant absolute pressure for the sample in the chamber. This constant absolute pressure stabilizes the operation of the sensor and thereby maintains a uniform indication of the percentage of oxygen in the breathable fluid above the predetermined altitude.

11 Claims, 2 Drawing Figures

OXYGEN MONITOR AND WARNING DEVICE FOR AN AIRCRAFT BREATHING SYSTEM

BACKGROUND OF THE INVENTION

In order to sustain the physiological well being of aircraft pilots required to breath oxygen and/or oxygen enriched air over long periods of time, recently developed aircraft breathing systems are equipped with hypoxia warning devices.

The most successful type of hypoxia warning device devised to date includes a polographic oxygen sensor. The polographic oxygen sensor continually monitors the partial pressure of oxygen in the breathable fluid supplied to the mask of the aircraft pilot. Should the oxygen level in the mask, as represented by the partial pressure, fall below a predetermined level, an alarm or indicator is activated to alert the pilot of a potential dangerous malfunction that could cause hypoxic conditions. Such polographic oxygen sensors provide a satisfactory warning for breathing systems in unpressurized aircraft cabins as long as the aircraft is below 28,000 feet in altitude. Unfortunately, in the event of decompression of the aircraft cabin above about 30,000 feet in altitude, the polographic oxygen sensor produces a warning signal due to a reduced total pressure even though the breathable fluid being supplied at that altitude is adequate.

SUMMARY OF THE INVENTION

We have devised a monitor and warning system having an aneroid arrangement for maintaining a minimum constant absolute pressure in a sample of breathable fluid which is supplied to a partial pressure oxygen sensor to provide a uniform analysis of the percentage of oxygen in a breathable fluid supplied to a pilot irrespective of the aircraft cabin pressure.

The aneroid arrangement has a housing with a chamber having an entrance port connected to the supply conduit through which the breathable fluid is supplied to the pilot and an exit port connected to the surrounding environment. A partial pressure sensor which extends into the chamber is exposed to the sample of breathable fluid as the sample flows to the surrounding environment through the exit port. An expandable aneroid attached to the housing has a face on the end thereof. The aneroid responds to changes in altitude and positions the face adjacent the exit port to restrict the flow of the breathable fluid to the environment. When the aircraft reaches a predetermined altitude, the face on the aneroid engages a seat on the housing surrounding the exit port to establish a minimum constant absolute fluid pressure in the chamber. Thereafter, as long as the aircraft remains above the predetermined altitude, analysis of the partial pressure of oxygen in the breathable fluid is unaffected by any decompression conditions induced into the cabin of the aircraft.

It is the object of this invention to provide an oxygen monitoring and warning system with an aneroid arrangement that causes an absolute pressure to be maintained in a sample of breathable fluid and thereby allows a sensor to uniformly analyze the partial pressure of the oxygen in a sample of breathable fluid without being effected by decompression in an aircraft cabin when the aircraft is above a predetermined altitude.

It is a further object of this invention to provide a breathing system with an oxygen monitoring and warning device that accurately analyzes the partial pressure of oxygen in a sample of breathable fluid throughout an entire operating altitude range of an aircraft.

It is another object of this invention to provide an oxygen monitoring and warning system with an aneroid arrangement that causes a minimum constant absolute fluid pressure to be produced in a sample of breathable fluid analyzed by a sensor to prevent the development of a false warning signal indicating an inadequate oxygen percentage in the breathable fluid.

These and other objects should be apparent from reading the specification and viewing the drawings.

DETAILED DESCRIPTION OF THE INVENTION

Figure 1:
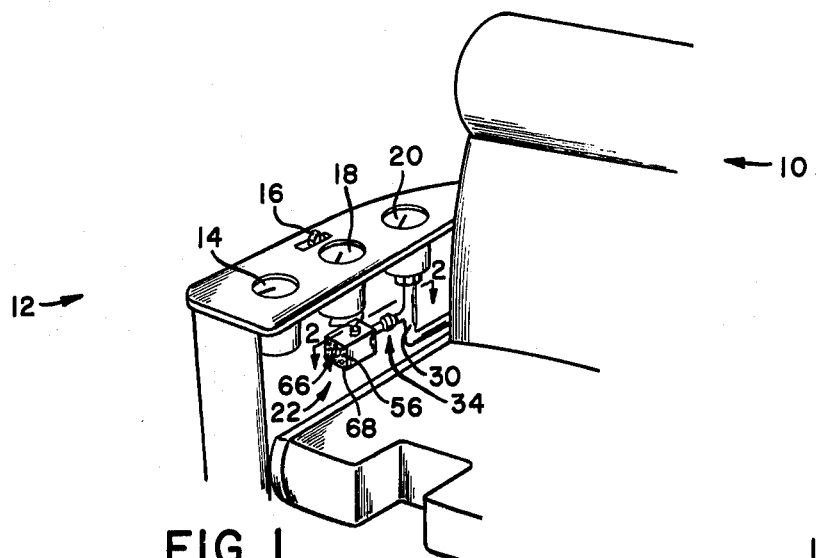
FIG. 1 is a schematic illustration of an oxygen monitor and warning system for a breathing system made according to the principles of this invention.

FIG. 1 illustrates a seat 10 and control panel 12 located in a cabin of an aircraft. The control panel 12 retains a pressure gauge 14 for measuring the atmospheric pressure in the aircraft cabin, an off-on switch 16 for supplying a breathing system with an operational or activation signal, a partial pressure gauge 18 connected to a sensor 22 for indicating the concentration of oxygen in the breathable fluid, and a supply pressure gauge 20 for indicating the pressure of the breathable fluid supplied to a recipient.

Figure 2:
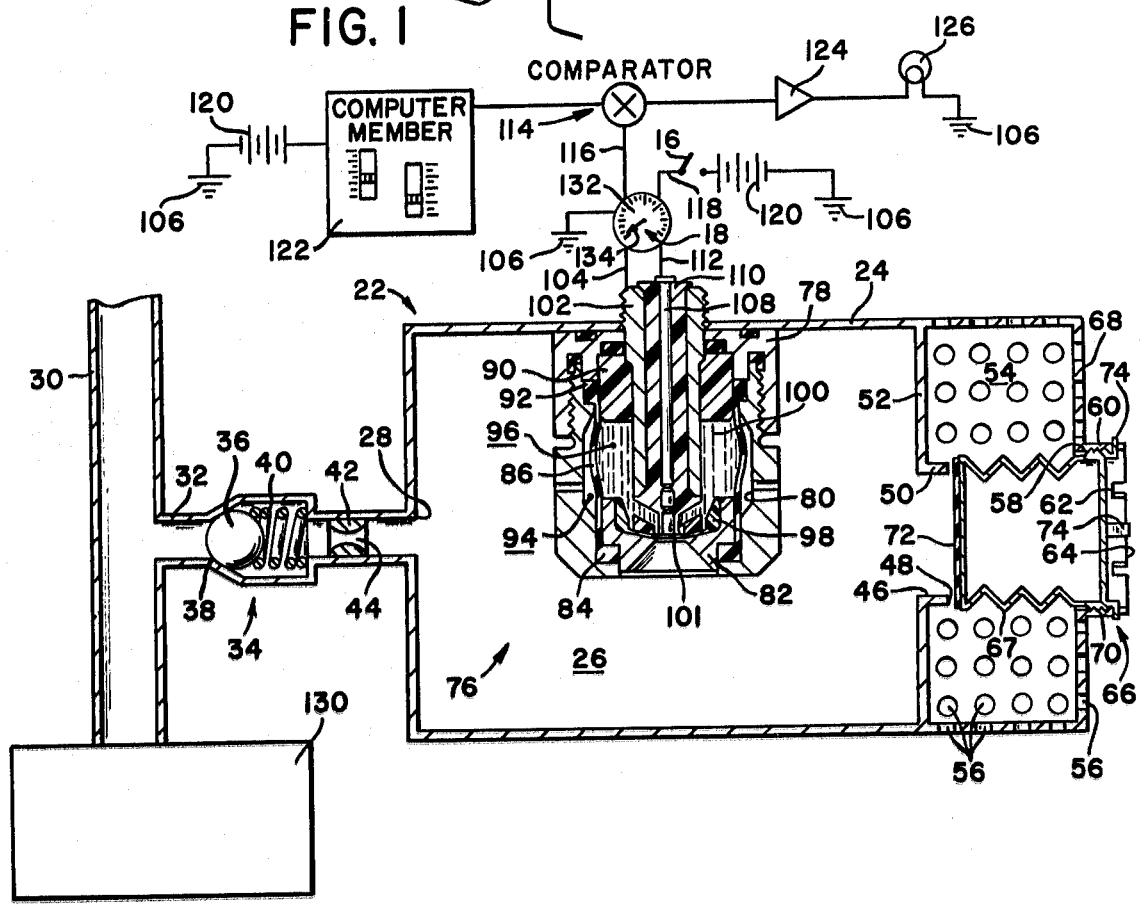
FIG. 2 is a sectional view taken along plane 2—2 of FIG. 1.

In more particular detail, the sensor 22, as shown in FIG. 2, has a housing 24 with a chamber 26 located therein. Chamber 26 has a first port 28 connected to the supply conduit 30 of the breathing system by a conduit 32. A check valve 34 located in conduit 32 has a poppet 36 urged toward a seat 38 by a spring 40 to prevent the flow of fluid from chamber 26 into supply conduit 30 and to maintain a minimum quantity of breathable fluid in the breathing system. A restrictive member 42 located in conduit 32 between the check valve 34 and port 28 has a fixed orifice 44 to limit the rate of flow of a sample of breathable fluid into chamber 26. Chamber 26 has an exit port 46 through which the sample of breathable fluid flows to the surrounding environment. A cylindrical member 50 attached to a wall 52 extends through port 46 to establish a seat 48 outside of chamber 26.

Wall 52 separates chamber 26 from an atmospheric chamber 54. The atmospheric chamber 54 is in free communication with the surrounding environment through the numerous perforations 56 in the housing 24.

Housing 24 has an opening 58 in alignment with port 46. A sleeve 60 located in opening 58 is fixed to the housing 24. Sleeve 60 has a series of slots 62 located adjacent end 64. An expandable bellows or aneroid member 66 is secured to the end 68 of housing 24 through a threaded connection 70. Face 72 is positioned a predetermined distance from seat 48 and tabs 74 moved into slots 62 to prevent further rotative movement of the aneroid member 66. The predetermined distance from seat 48 to face 72 can be checked for accuracy and if the expansion of the bellows 67 does not move face 72 to a preset distance from seat 48 at a predetermined altitude, an adjustment is made by moving tabs 74 from slots 62 and rotating the aneroid member 66 until the distance between seat 48 and face 72 match the expansion of aneroid 67. It should be noted that the area of port 46 is equal to the effective area of face 72 on the aneroid 67. Thus, as the aircraft increases in altitude, the fluid pressure in sample of breathable fluid is correspondingly maintained at a minimum absolute pressure in chamber 26.

An oxygen sensor 76 that responds to the partial pressure of oxygen in a breathable fluid is attached to housing 24. The oxygen sensor 76 has a housing 78 with a bore 80 therein. A ring member 82 holds a first end 84 of a diaphragm 86 against the housing 78 while a sleeve 90 holds a second end 92 against the housing to establish first and second chambers 94 and 96 within bore 80. A polytetrafluoroethylene membrane 98 of either flourinated ethylene tropolone or polytetrafluoroethylene is located adjacent to the ring member 82 to retain an electrolyte gel 100 such as potassium chloride in chamber 96. The polytetraflouroethylene membrane 98 has a relatively thin surface 101 and compresses the gel electrolyte 100 beneath it into a very thin film. The polytetrafluoroethylene membrane 98 is permeable to oxygen but prevents the transmission of airborne solids or liquid contaminants to the electrolyte gel. A silver anode 102 which extends through sleeve 90 into chamber 96 is connected by lead 104 to gauge 18 and ground 106. A gold cathode 108 which is concentrically positioned with respect to the sliver anode 102 by a nonelectrical conductive sleeve 110. The gold cathode 108 is connected to gauge 18 by lead 112. Gauge 18 is connected to a comparator 114 by lead 116 and to an electrical energy source such as battery 120 by lead 118.

The comparator 114 is connected to a computer member 122. Computer member 122 supplies comparator 114 with a reference signal indicative of the minimum physiological oxygen level required by a recipient at a given altitude. The comparator 114 is connected through amplifier 124 to a light 126 or other indicator such as a bell, buzzer, etc. When an operational signal from gauge 18 differs from the reference signal, the light 126 or other indicator is activated to inform the pilot of a potentially dangerous condition that could product hypoxia.

MODE OF OPERATION OF THE INVENTION

When an aircraft pilot desires to receive breathable fluid from a source 130, switch 16 is activated. Switch 16 operates a valve to allow the breathable fluid to flow in conduit 30. Conduit 30 is attached to a flow regulator (not shown) which controls the flow of breathable fluid to the pilot.

The pilot by glancing at the instrument panel 12 can immediately read on gauge 20 the pressure at which the breathable fluid is being presented to the regulator.

At the same time a sample of the breathable fluid is bled off of conduit 30 by flowing past check valve 34 in conduit 32 for presentation to the oxygen sensor 76 in chamber 26. The sample of breathable fluid in chamber 26 continually changes since port 46 is opened to the surrounding environment through chamber 54.

The oxygen in the sample of breathable fluid passes through the thin surface 101 of fluorinated ethylene tropolone or the polytetrafluoroethylene membrane 98 and reacts with the electrolyte gel 100 (i.e., potassium chloride) to allow an electrical signal to flow between the silver anode 102 and gold cathode 108. This electrical signal is transmitted to gauge 18 and is displayed by pointer 134 on dial 132 as the percentage of oxygen in the breathable fluid.

The electrical signal that drives pointer 134 is also transmitted to comparator 114. As long as the reference signal from the computer member 122 is larger than or equal to the electrical signal, light 126 remains deenergized. However, should a malfunction occur in the generation or distribution system of the breathable fluid and the percentage of oxygen be insufficient to maintain an adequate physiological operational level for the pilot, the partial pressure electrical signal created in sensor 76 that drives pointer 134 would be less than the reference signal. Thereafter, an imbalance would occur in the comparator and a warning signal would be transmitted from amplifier 124 sufficient to operate light 126 and inform the pilot of this potentially dangerous condition.

As the aircraft changes altitude, expandable aneroid 67 follows a curve similar to the increase in oxygen needs of the pilot. The expansion of aneroid 67 moves face 72 toward seat 48 to restrict the flow of sample breathable fluid from chamber 26. When the aircraft rises to a predetermined altitude, face 72 engages seat 48 to meter the flow of the sample breathable fluid from chamber 26 and thereafter develop a fixed or constant absolute fluid pressure for the sample in chamber 26. Thereafter, pressure conditions under which the sample of breathable fluid and the measurement of the partial pressure of the oxygen therein is constant. Thus, the sensor 76 accuracy in the measurement of the percentage of oxygen in the breathable fluid is unaffected by any changes in the pressure conditions of the cabin induced by the operation of the aircraft.

We claim:

1. In an aircraft breathing system having a sensor for monitoring the concentration of oxygen in a source of breathable fluid supplied to a recipient, means for developing a minimum constant absolute pressure in a sample of breathable fluid to maintain the accuracy of the sensor within acceptable limits above a predetermined altitude, said means comprising:

a housing having a chamber therein, said chamber being connected to said sensor, said chamber having a first port connected to said source of breathable fluid and a second port connected to the surrounding environment, said sample of breathable fluid flowing through said chamber to the surrounding environment to provide said sensor with a continuous indication of the breathable fluid supplied to said recipient; and aneroid means for restricting the flow of the breathable fluid through said second port as a function of altitude to establish said minimum constant absolute pressure in said sample.

2. In the aircraft breathing system as recited in claim 1 further including:

a valve located between said source of breathable fluid and said first port to prevent the back flow of breathable fluid from the chamber into source of breathable fluid supplied to the recipient.

3. In the aircraft breathing system as recited in claim 2 further including:

an orifice member associated with said first port to establish a fixed flow rate into said chamber for said sample of breathable fluid.

4. In the aircraft breathing system as recited in claim 3, wherein the effective closure area of the aneroid means and the second port are equal, said closure area engaging said second port above said predetermined altitude to maintain a constant pressure in said chamber as the flow of sample breathable fluid is metered to the surrounding environment.

5. In a breathing system, an oxygen monitoring and warning device comprising:

a housing having a chamber therein with an entrance port, an exit port, and a sensor port;

a sensor connected to said sensor port and responsive to the partial pressure of oxygen in the breathable fluid in said chamber for creating an operational signal;

a conduit attached to said entrance port and connected to a supply of breathable fluid communicated to a recipient for continually transmitting a sample of breathable fluid to said chamber, said sample of breathable fluid flowing through said exit port to the atmosphere to provide said sensor with a substantially instantaneous indication of the breathable fluid supplied to the recipient; and aneroid means connected to said housing for restricting the flow of breathable fluid from said chamber through said exit port as a function of altitude to maintain a substantially constant absolute fluid pressure in the sample of breathable fluid and thereby maintain the usefulness of said sensor above a predetermined altitude.

6. In the breathing system, as recited in claim 5 further including:

an orifice member located in said conduit to establish a fluid flow rate for the communication of the sample into said chamber.

7. In the breathing system, as recited in claim 6 further including:

a check valve located in said conduit to prevent contamination of said supply of breathable fluid from the flow of fluid from the surrounding environment.

8. In the breathing system as recited in claim 7 further including:

adjustment means for changing the position of a face on said aneroid means and a seat surrounding said exit port to match the engagement of the face and the seat at said predetermined altitude.

9. In the breathing system, as recited in claim 8 further including:

an indicator connected to said sensor and responsive to said operational signal for providing said recipient with a reading of the percentage of oxygen in the breathable fluid.

10. In the breathing system, as recited in claim 7 wherein said check valve maintains a residual quantity of breathable fluid in the conduit during periods of none use of the breathing system.

11. In the aircraft breathing system, recited in claim 2 wherein said valve means prevents a minimum quantity of breathable fluid from being communicated to the surrounding environment during periods of none use of the breathing system.

* * * * *